United States Patent [19]
Eek

[11] Patent Number: 5,856,342
[45] Date of Patent: Jan. 5, 1999

[54] COMBINATION OF A β-RECEPTOR BLOCKER AND A LOCAL ANAESTHETIC

[75] Inventor: Arne Eek, Trosa, Sweden

[73] Assignee: Astra AB, Sweden

[21] Appl. No.: 428,170

[22] PCT Filed: Apr. 24, 1995

[86] PCT No.: PCT/SE95/00314

§ 371 Date: Apr. 28, 1995

§ 102(e) Date: Apr. 28, 1995

[87] PCT Pub. No.: WO95/27511

PCT Pub. Date: Oct. 19, 1995

[30] Foreign Application Priority Data

Apr. 7, 1994 [SE] Sweden .................................. 9401174

[51] Int. Cl.$^6$ ................................................. A61K 31/445
[52] U.S. Cl. ......................... 514/330; 514/626; 514/652; 514/817; 514/818
[58] Field of Search ............................. 514/78, 626, 817, 514/818, 330, 652

[56] References Cited

U.S. PATENT DOCUMENTS 5,496,811  3/1996  Aviv et al. ................................ 514/78

FOREIGN PATENT DOCUMENTS 1 277 601   6/1972   United Kingdom ........... A61K 27/00

OTHER PUBLICATIONS

Machtens et al., "Qualitative Probleme der Schmerzausschaltung durch kombinierte Gabe von beta–adrenolytischen Substanzen mit Lokalanästhetika," *Dtsch. zahnärztl. Z.* 28:1021–1025 (1973).

Capucci et al., "Tocainide and Metoprolol: An Efficacious Therapeuric Combination in the Treatment of Premature Ventricular Beats," *Clin. Cardiol.* 12:322–331 (1989).

Chemical Abstracts AN 1987:417566, Coram et al., Jan. 1987.

*Primary Examiner*—Keith D. MacMillan
*Attorney, Agent, or Firm*—Michael A. Sanzo; Vinson & Elkins L.L.P.

[57] ABSTRACT

New combination of a β-receptor blocker, an enantiomer thereof, and a local anesthetic, administered simultaneously or sequentially, giving excellent pain relief. Also comprised in the invention is the use of a non-selective β-receptor blocker alone, especially a non-selective β-receptor blocker giving pain relief.

45 Claims, No Drawings

COMBINATION OF A β-RECEPTOR BLOCKER AND A LOCAL ANAESTHETIC

This application is a 371 of PCT/SE95/00314, filed Mar. 24, 1995.

FIELD OF THE INVENTION

The present invention is related to improvements in pain relief. More particularly it relates to the use of β-receptor blockers, especially alprenolol and metoprolol, or a pharmaceutically acceptable salt thereof, alone or in combination with a local anaesthetic or a pharmaceutically acceptable salt thereof, for the treatment of pain, and to pharmaceutical compositions containing the two active ingredients.

BACKGROUND OF THE INVENTION

Pain is maybe the most feared and disabling consequence of illness and trauma. It is also the most frequent reason why patients seek medical consultation. It has been estimated that pain costs the US economy at least 600 BSEK (billion Swedish crowns). Only recently this enormous and costly human suffering has obtained significant attention among the medical community and researches. The attention will continue to grow as the great therapeutic need is obvious, pain increases as population ages. Pain research has recently made major progress.

Some examples of pain indications are postoperative pain, diabetic neurophathia and cancer pain.

Postoperative Pain

Postoperative pain is one of the most frequent types of acute pain and generally undertreated. Thus, 80.000 surgical procedures per million inhabitants take place per year and 75% suffer from postoperative pain.

Postoperative pain may be regarded as a specific variant of acute nociceptive pain. It is markedly different from cancer pain, chronic pain and neurogenic pain in pathophysiology, psychological correlation and therapeutic approaches.

| Operative site | Severe pain | Moderate pain | Mild pain |
| --- | --- | --- | --- |
| Thoracic | 50 | 40 | 10 |
| Upper/lower abd | 35 | 45 | 20 |
| Joints/orthopedic | 60 | 30 | 10 |
| Spine | 25 | 50 | 25 |
| Superficial head, neck, chest | 20 | 35 | 45 |
| TOTAL (%) | 40 | 30 | 30 |

Apart from the humanitarian aspects of relieving pain after surgery, there are physiological benefits to the patients.

Adverse effects of poorly controlled pain include:

Decreased respiratory movement, contributing to hypoxia and atelectasis after operation.

Decreased mobility, increasing the risk of deep venous thrombosis formation, slow intestinal motility and muscular wasting.

Increased sympathetic activity possibly resulting in hypertension and myocardial ischemia.

Increased hormonal and metabolic activity.

Diabetic Neuropathy

A causal and effective therapy of diabetic neuropathy does not yet exist and currently available therapy offers limited success and unacceptable side effects. Neuropathy develops in more than two thirds of the diabetic patients in the course of the disease. The prevalence usually vary between 12% and 50% and the incidence and severity vary with age, duration of diabetes and possibly the quality of glycaemic control. The number of patients suffering from painful diabetic neuropathy in North America is estimated to be 2 millions. One of many problems caused by diabetes is nerve damage. This may result in pain that is insidious, sudden and acute, or a mixture of these traits.

Cancer Pain

The incidence of cancer has increased steadily for 20 years. In Sweden and in the US it is now 0.45% or 4500/million inhabitants and year who are taken ill in cancer. In the age group 60 years old it is 1% and then increases to 3% for 80 years old men. The incidence of cancer that causes severe pain is 0.16% or 1600 cases/million inhabitants per year, and 1.3 million worldwide.

Most cancer patients live for several years with their disease. Pain accompanies the disease most of the time and is frequently the original cause for consulting a medical doctor. The life expectancy of patients with advanced or terminal cancer varies from a few months to a few years. It has been found that the prevalence of pain in these patients varies between 55 and 90%, average 75%, depending mostly on the site of cancer.

Current Therapies

The Need of Qualified Pain Relief

The standard treatment for postoperative pain following major abdominal and orthopedic surgery consists normally of repeated injections of an opioid such as morphine given by ward nurses on request. This is generally recognized as an inferior technique since there is reluctance to administer the doses in the individual manner that both the pharmacokinetic and pharmacodynamic variation will require. Usually, standard regimens are too little too seldom, whereby many patients never reach satisfactory analgesia while others may suffer from overdosage, i.e. only a few receive satisfactory postoperative pain relief.

The sole use of opioids is generally effective, but has a wide range of side effects such as early or late respiratory depression, intestinal paralysis, bladder dysfunction and pruritus. Epidural analgesia is more and more provided by a combination of local anaesthetics and opioids.

Apart from providing excellent analgesia, the use of local anaesthetics have benefits such as reduced incidence of deep vein thrombosis, improved gastrointestinal mobility, improved ventilatory function with less atelectasis formation or pneumonia. The use of an epidural block has been shown to decrease the hormonal response to trauma, however, the clinical benefits of this is not entirely unambiguous.

The main side effect of spinally administered local anaesthetics is hypotension related to the extent of sympathetic blockade. Other side effects following epidural analgesia with local anaesthetics are muscle weakness and difficulties with micturation.

Local anaesthetics may be combined with opioids for per- and postoperative epidural use. This combination gives a greater separation between the analgesic properties and the motor blockade than following continuous administration of local anaesthetics alone. Although the combination provides superior pain relief, the introduction of opioids adds new side-effects. The most feared is late respiratory depression that may occur up to more than 24 hours after spinal administration. Elderly patients are more susceptible, but respiratory depression has also been seen in young, healthy patients.

Current Therapy—Diabetic Neuropathic

Several pharmacological agents e.g. phenytoin, carbamazepine, phenothiazines, anaesthetics and amitriptyline have proven beneficial in patients. OTC analgesics and NSAID's are often inactive.

The drug of choice is probably amitriptyline as it reduces burning, aching, sharp, throbbing and stinging pain. In many instances medication with antidepressants, anticonvulsants etc gives side effects that are unacceptable, especially in elderly, thus limiting the potential benefit. Pain relief requires 2–4 weeks of therapy or more.

Current Therapy—Cancer Pain

In many cases chemotherapy and/or radiotherapy in conjunction with surgical procedures can relieve pain symptoms. Symptomatic analgesic therapy is, however, necessary in the vast majority of cancer patients. Drug treatment follows the standard analgesic ladder using NSAID's paracetamol, and opioids.

Adjuvant drugs such as corticosteroids, bisphosphonates, benzodiazepins, and anticonvulsants are often used.

A minor group, relatively, is not helped by these treatments. The number of patients in need of advanced pain treatment, sometimes non-drug methods, is around 10–15% of all patients, who experience severe pain. In the remaining 5% pain control is unsatisfactory using any drug or advance technique available.

The above figures do not mean that 80–90% of all patients obtain proper pain relief. On the contrary, many reports state that as many as 30–40% suffer from insufficient pain relief due to undertreatment. Fear of side effects (nausea, sedation, constipation, pruritus) and addiction, and poor knowledge of proper drug use play great roles. Of course, oral systemic administration is most often used but intravenous administration of opioids is common in the hospital. The use of patient controlled analgesia (PCA) can be handled in tha pain clinic and is gaining wider acceptance.

Terminal cancer patients are treated for longer periods in the hospital or hospice where advanced pain treatment is available. A striking figure from 1988 is that 7% of all days of hospital care in Sweden were caused by tumour disease as major diagnosis. A relative large proportion of the cancer patients are thus amenable to advanced pain treatment.

Regional analgesia using either local anaesthetics, for prompt relief of unbearable pain, or opioids, given intrathecally or epidurally, is sometimes used. The technique has gained in popularity and the benefits of intraspinal opioids might even facilitate patient care at home, leading to a higher quality of life.

Von E. Machtens et al., discloses in Deutsche Zahn ärzlicke Zeitschrift, 28 (1973): 10, p. 1021–1025, a combination of alprenolol and xylocaine. The problem the authors achieve to solve by the combination, is increased anaesthetic properties, whereas the problem solved according to the present invention is to reduce the concentration of the local anaesthetic to avoid motor blockade. The present invention solves this problem by the combination of a local anaesthetic, lidocaine being disclaimed, and a β-receptor blocker.

OUTLINE OF THE INVENTION

The present invention is based on the concept of a novel combination therapy, whereby a β-receptor blocker or a physiologically and pharmaceutically acceptable salt thereof, and a local anaesthetic or a physiologically and pharmaceutically acceptable salt thereof, are administered simultaneously, sequentially or in form of a pharmaceutical composition comprising the two active ingredients, together with a pharmaceutical acceptable carrier.

Examples of β-receptor blockers which can be used for the combination therapy according to the invention, are alprenolol which has the formula

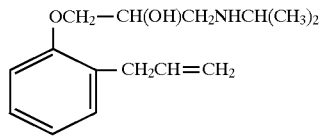

propanolol which has the formula

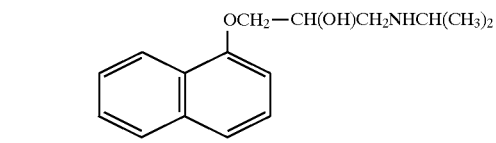

and pindolol which has the formula

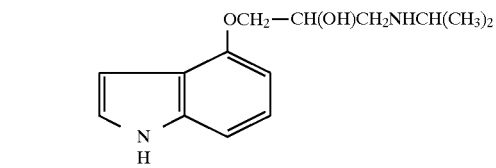

The above mentioned β-receptor blockers are non-selective β-receptor blockers.

Also selective β-receptor blockers can be used for the combination therapy according to the invention. One example of a selective β-receptor blocker with advantageous effects in the combination therapy with a local anaesthetic is metoprolol, which has the formula

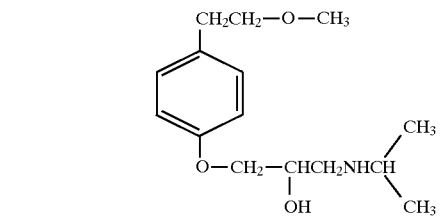

Alprenolol is especially preferred as the β-receptor blocker but any suitable β-receptor blocker is possible to use and said examples of β-receptor blockers are however not in any way exhaustive.

The local anaesthetic can be any of ropivacaine, bupivacaine, mepivacaine or tocainide among others, or a pharmaceutically acceptable salt thereof.

In a preferred embodiment alprenolol is used in combination with ropivacaine as the local anaesthetic. In an especially preferred embodiment the alprenolol racemate is used in the combination with ropivacaine.

An advantage with the present invention is that by using the combinations mentioned above in the management of pain, the side-effects associated with the opiates which usually are used for the treatment of pain are avoided. It is according to the present invention possible to avoid the motor block effect, only having the sensoric block, which is very advantageous in many aspects.

The compounds used according to this invention may be administered in the form of free bases or their pharmaceutically acceptable salts with non-toxic adds. Some typical examples of these salts are the hydrochloride, citrate, tartrate, bensoate and succinate. Especially preferred is the bensoate, tartrate and succinate.

The way of administration can be orally, intramuscularly, intravenously, spinally, epidurally, by inhalation or nasally, among others.

The concentration of the β-receptor blocker may be in the range 0.20–120 μmol/ml, preferably 0.20–30 μmol/ml.

The concentration of the local anaesthetic may be in the range 0.20–120 μmol/ml, preferably in the range 0.20–30 μmol/ml.

It has now unexpectedly been found that β-receptor blockers, especially alprenolol, in combination with a local anaesthetic, in doses devoid of apparent motor impairment or sedation, give a supra-additive effect or synergy effect in the management of pain. The local anaesthetic ropivacaine which is described in WO 8500599, in form of its hydrochloride, is together with the compound alprenolol excellent in the treatment of pain. It has even surprisingly been found that local anaesthetics generally, have this synergy effect in combination with β-receptor blockers.

Pharmaceutical Preparations

In clinical practice the active ingredients are administered simultaneously or sequentially, either one after another, or in form of a pharmaceutical preparation containing the two active ingredients, either as a free base or as a pharmaceutically acceptable non-toxic, acid addition salt, e.g. the hydrochloride, hydrobromide, lactate, acetate, sulphate, sulphamate and the like together with a pharmaceutically acceptable carrier. The way of administration is normally spinally, epidurally, intravenously, intramuscularly, orally or rectally among others. Administration spinally and epidurally is especially preferred.

Accordingly, terms relating to the novel combinations of this invention whether generically or specifically are intended to include both the free amine base and the add addition salts of the free base, unless the context in which such terms are used, e.g. in the specific examples would be inconsistent with the broad concept. The carrier may be a solid, semisolid or liquid diluent or capsule. These pharmaceutical preparations constitute a further aspect of this invention. Usually the amount of active substance will constitute between 0.1 and 99% by weight of the preparation, more specifically between 0.5 and 20% by weight for preparation intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g., lactose, saccharose, sorbitol, mannitol, starches such as potato starch, corn starch, amylopectin, laminaria powder or citrus pulp powder, cellulose derivatives, or gelatin, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g., gum arabic, gelatin, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and e.g. glycerol, the active substance may be admixed with a vegetable oil. Hard gelatin capsules may contain granulates of the active substance in combination with solid, pulverulent carriers such as lactose, saccharose, sorbitol, mannitol, starches (e.g., potato starch, corn starch or amylopectin), cellulose derivatives or gelatin.

Dosage units for rectal application can be prepared in the form of suppositories comprising the active substance in admixture with a neutral fatty base, or gelatin rectal capsules comprising the active substance in admixture with vegetable oil or paraffin oil.

A pharmaceutical preparation for infusion was prepared, according to the following.

Solution for Injection—1 mg/ml

Alprenolol hydrochloride for injection 1 g

Sodium chloride for injection 9 g

A solution of alprenolol is prepared in sterile $H_2O$ for injection and pH adjusted with sodium hydroxide to pH 7.1.

Pharmaceutical Preparations of Ropivacaine

EXAMPLES 1–3

Solution 5 mg/ml, 3 mg/ml, 2 mg/ml

| | Examples | | |
|---|---|---|---|
| | 1 | 2 | 3 |
| Ropivacaine hydrochloride monohydrate | 0.53 kg | 0.32 kg | 0.21 kg |
| Purified water qs ad | 100 kg | 100 kg | 100 kg |

Ropivacaine is dissolved in the water. Sodium hydroxide is added to pH 5.0–6.0. The resulting solution is autoclaved.

Biological Tests

Tests according to the tail-flick model were performed, where the sensoric and motoric effects of the combinations of different local anaesthetics, and alprenolol and propanolol respectively, and the synergistic effects of these were studied.

The purpose with these studies was to show the synergistic effect in pain management, achieved when combining a local anaesthetic and a β-receptor blocker, especially alprenolol, propanolol, metoprolol (R), metoprolol (S) and metoprolol racemate.

Dosing

Intrathecal injections in the mice were performed essentially according to Hylden and Wilcox (Hylden Jl, Wilcox GL, Intrathecal morphine in mice: a new technique., Eur J Pharmacol 1980; 67:313–6). A 30-G cannula was inserted between the L5 and L6 vertebrae following a small incision of the skin over this region. The different solutions were injected in a volume of 5 μl of a β-receptor blocker or 5 μl of a local anaesthetic, or 5 μl of a mixture of a β-receptor blocker and a local anaesthetic.

Antinociception

The animals were tested for tail-flick (Åkerman B, Arweström E, Post C, Local anaesthetics potentiate spinal morphine antinociception, Anesth Analg 1988; 67:943–8) reaction latencies before administration of the test compounds (pre-drug value) and 5 minutes after disappearance of the motor block. Thereafter, testing was performed every 15 minutes until the pre-drug latencies were obtained. In the tail-flick test, a thermostat-controlled light beam was directed at the tip of the tail (IITC Inc Model 33). The latency to a flick of the tail was measured and a cut-off time of 10 seconds was used. Signs of adverse effects of the test compounds were recorded. Frequency, onset and duration of motor block after intrathecal injection of 5 μl of the β-receptor blocker or 5 μl of the local anaesthetic, or 5 μl of a mixture of a β-receptor blocker and a local anaesthetic to male mice were tested. Motor block was defined as the inability of the mouse to stand on its hind limbs and recovery was regarded as having occured when the mouse could walk and grip the floor normally.

Test Compounds and Solutions

Alprenolol racemate was used in a concentration of 3.75–60 μmol/ml. Ropivacaine was used in a concentration of 7.5–60.0 μmol/ml. Mepivacaine was used in a concentration of 15.0–120 μmol/ml. Bupivacaine was used in a concentration of 3.75–30.0 μmol/ml and tocainide was used in a concentration of 15.0–120.0 μmol/ml. All solutions were prepared at Astra AB in saline 9.0 mg/ml.

The best mode of performing the present invention known at present, is to use alprenolol in combination with ropivacaine.

EXAMPLE 1

Test for Synergistic Effect

The sensoric effect of a combination of alprenolol racemat with ropivacaine on tail-flick latency in mice.

Each concentration was tested on groups of 6 animals.

TABLE 1

| Alprenolol | | Ropivacaine | | Alprenolol + Ropivacaine | |
|---|---|---|---|---|---|
| μmol/ml | sec. | μmol/ml | sec. | μmol/ml + μmol/ml | sec. |
| 3.75 | 4.65 | — | — | 3.75 + 1.88 | 4.49 |
| 7.50 | 8.34 | 7.50 | 4.39 | 3.75 + 3.75 | 5.43 |
| 15.00 | 10.00 | 15.00 | 8.05 | 3.75 + 7.50 | 10.00 |
| 30.00 | 10.00 | 30.00 | 10.00 | | |

A solution with a concentration of 15 μmol/ml of alprenolol singel and a solution of a concentration of 30 μmol/ml of ropivacaine singel gave 100% sensoric effect.

When these two substances were given in combination, an amount of only 3.75 μmol alprenolol and 7.5 μmol of ropivacaine was required to achieve 100% sensoric effect. This means that there is only required an amount of ropivacaine which is one fourth (¼) and an amount of alprenolol which is one fourth (¼) required to achieve 100% effect, compared to the amount required when these substances are given separately. These two substances given in combination confers a synergistic effect in antinociceptive treatment.

EXAMPLE 2

The test was performed in exactly the same way as in Example 1, but the concentration of alprenolol when given in combination with ropivacaine was held constantly at 7.50 μmol/ml.

TABLE 2

| Alprenolol | | Ropivacaine | | Alprenolol + Ropivacaine | |
|---|---|---|---|---|---|
| μmol/ml | sec. | μmol/ml | sec. | μmol/ml + μmol/ml | sec. |
| 3.75 | 4.65 | 7.50 | 4.39 | 7.50 + 0.94 | 9.13 |
| 7.50 | 8.34 | 15.00 | 8.05 | 7.50 + 1.88 | 9.18 |
| 15.00 | 10.00 | 30.00 | 10.00 | 7.50 + 3.75 | 9.19 |
| 30.00 | 10.00 | — | — | 7.50 + 7.50 | 10.00 |

When alprenolol was given in the combination, an amount of 7.50 μmol/ml of alprenolol and 7.50 μmol/ml of ropivacaine was required to achieve 100% sensoric effect.

EXAMPLE 3

The sensoric effect of the combination of alprenolol and mepivacaine on tail-flick latency in mice was tested. Each concentration was tested on groups of 6 animals.

TABLE 3

| Alprenolol | | Mepivacaine | | Alprenolol + Mepivacaine | |
|---|---|---|---|---|---|
| μmol/ml | sec. | μmol/ml | sec. | μmol/ml μmol/ml | sec. |
| 3.75 | 4.65 | 15.0 | 4.24 | 3.75 + 15.0 | 7.01 |
| 7.5 | 8.34 | 30.0 | 5.91 | 7.50 + 15.0 | 10.00 |
| 15.0 | 10.00 | 60.0 | 4.31 | 15.0 + 15.0 | 10.00 |
| 30.0 | 10.00 | 120.0 | 10.00 | | |
| — | — | | | | |

A solution of a concentration of mepivacaine singel of 120 μmol/ml gave 100% sensoric block. To achieve the same effect with alprenolol singel a solution of a concentration of 15.0 μmol/ml was required. When these two substances were given in combination there was only required one half (½) of the dose of alprenolol and one eighth (⅛) the amount of the dose of mepivacaine to achieve 100% sensoric block. This shows that a synergistic effect is present when alprenolol and mepivacaine is given in combination.

EXAMPLE 4

The sensoric effect of the combination of alprenolol and bupivacaine on tail-flick latency in mice was tested on groups of 6 animals.

TABLE 4

| Alprenolol | | Bupivacaine | | Alprenolol + Bupivacaine | |
|---|---|---|---|---|---|
| μmol/ml | sec. | μmol/ml | sec. | μmol/ml μmol/ml | sec. |
| 3.75 | 4.65 | 3.75 | 5.44 | 3.75 + 0.94 | 4.71 |
| 7.50 | 8.34 | 7.50 | 8.13 | 3.75 + 1.88 | 8.39 |
| 15.00 | 10.00 | 15.00 | 6.98 | 3.75 + 3.75 | 10.00 |
| 30.00 | 10.00 | 30.00 | 10.00 | — | — |

A solution with a concentration of 15 μmol/ml of alprenolol singel and 30 μmol/ml of bupivacaine singel gave 100% sensoric block. When these two substances were given in combination, there was only required 3.75 μmol/ml of alprenolol and 3.75 μmol/ml of bupivacaine to achieve 100% sensoric block. This shows that the combination of alprenolol and bupivacaine confers a synergistic effect.

EXAMPLE 5

This test was performed as described in the previous examples.

TABLE 6

| Alprenolol | | Tocainide | | Alprenolol + Tocainide | |
|---|---|---|---|---|---|
| μmol/ml | sec. | μmol/ml | sec. | μmol/ml μmol/ml | sec. |
| 3.75 | 4.65 | 15.0 | 4.79 | 1.88 + 30.00 | 6.02 |
| 7.50 | 8.34 | 30.0 | 5.48 | 3.75 + 30.00 | 8.31 |
| 15.00 | 10.00 | 60.0 | 6.74 | 7.50 + 30.00 | 10.00 |
| 30.00 | 10.00 | 120.0 | 10.00 | | |

A solution with a concentration of 15 μmol/ml of alprenolol singel gave 100% sensoric block. The concentration of tocainide singel was 120.0 μmol/ml to achieve the same result.

When these two substances were given in combination, there was only required 7.50 μmol/ml of alprenolol and 30.00 μmol/ml of tocainide to achieve 100% sensoric block.

EXAMPLE 6

The sensoric effect of a combination of the (R)-enantiomer of metoprolol with ropivacaine was tested in exactly the same way as in the previous examples.

TABLE 7

| Metoprolol R(+) klorid | | Ropivacaine | | Metoprolol R(+) + Ropivacaine | |
|---|---|---|---|---|---|
| μmol/ml | sec. | μmol/ml | sec. | μmol/ml μmol/ml | sec. |
| 30 | — | — | — | 3.75 + 7.50 | 6.55 |
| 60 | 4.97 | 7.50 | 4.39 | 7.50 + 7.50 | 8.38 |
| 90 | 7.64 | 15.00 | 8.05 | 15.00 + 7.50 | 8.91 |
| 120 | 8.58 | 30.00 | 10.00 | 30.00 + 7.50 | 10.00 |

A solution with a concentration of 120 μmol/ml of metoprolol (R)-enantiomer chloride gave a 85.8% sensoric effect, and a solution of a concentration of 30.00 μmol/ml of ropivacaine singel gave 100% sensoric effect.

When these two substances were given in combination an amount of 30.00 μmol of metoprolol (R) hydrochloride and 7.5 μmol/ml of ropivacaine was required to achieve 100% sensoric effect. This shows that the combination of metoprolol (R) and ropivacaine confers a synergistic effect.

EXAMPLE 7

The sensoric effect of a combination of the (S)-enantiomer of metoprolol with ropivacaine was tested in exactly the same way as in the previous examples.

TABLE 8

| Metoprolol S(−) klorid | | Ropivacaine | | Metoprolol S(−) + Ropivacaine | |
|---|---|---|---|---|---|
| μmol/ml | sec. | μmol/ml | sec. | μmol/ml μmol/ml | sec. |
| 30 | — | — | — | 7.5 + 7.5 | 5.23 |
| 60 | 4.45 | 7.50 | 4.39 | 15.0 + 7.5 | 6.84 |
| 120 | 6.31 | 15.00 | 8.05 | 30.0 + 7.5 | 10.00 |
| 240 | 10.00 | 30.00 | 10.00 | 60.0 + 7.5 | 10.00 |

A solution with a concentration of 240 μmol/ml of metoprolol (S)-enantiomer chloride singel and a solution of a concentration of 30.00 μmol/ml of ropivacaine singel gave 100% sensoric effect.

When these two substances were given in combination, an amount of only 30.0 μmol/ml of metoprolol (S) and 7.5 μmol/ml of ropivacaine was required to achieve 100% sensoric effect. This shows that the combination of metoprolol (S) and ropivacaine confers a synergistic effect.

Results

The studies performed and described according to the present invention show that there is a synergistic effect when a local anaesthetic and β-receptor blocker is given in combination. The results also show that a β-receptor blocker given alone, especially alprenolol, has a positive effect in relieving pain.

The β-receptor blocker can be supplied together with a local anaesthetic, and optionally additional agents, in form of a kit.

I claim:

1. A pharmaceutical composition for achieving essentially complete sensory block in a patient without substantial motor block, comprising a β-receptor blocker and a local anesthetic, wherein:

a) said β-receptor blocker is present at a concentration sufficient to produce essentially complete sensory block when administered to said patient in combination with said local anesthetic; and
b) said local anesthetic is present at a concentration:
   i) sufficient to produce essentially complete sensory block in said patient when administered in combination with said β-receptor blocker; and
   ii) lower than the concentration needed to produce essentially complete sensory block in said patient when said local anesthetic is administered as the sole therapeutically active agent;
with the proviso that said local anesthetic is not lidocaine.

2. The pharmaceutical composition of claim 1, wherein said β-receptor blocker is a non-selective β-receptor blocker.

3. The pharmaceutical composition of claim 1, wherein said β-receptor blocker is a selective β-receptor blocker.

4. The pharmaceutical composition of claim 1, wherein said β-receptor blocker is present at a concentration lower than that needed to produce essentially complete sensory block when said β-receptor blocker is administered as the sole therapeutically active agent.

5. The pharmaceutical composition of either claim 1 or claim 4, wherein said β-receptor blocker is alprenolol.

6. The pharmaceutical composition of either claim 1 or claim 4, wherein said β-receptor blocker is R(+) metoprolol.

7. The pharmaceutical composition of either claim 1 or claim 4, wherein said β-receptor blocker is S(−) metoprolol.

8. The pharmaceutical composition of either claim 1 or claim 4, wherein said local anesthetic is selected from the group consisting of: ropivacaine, mepivacaine, bupivacaine, and tocainide.

9. The pharmaceutical composition of claim 1, wherein said local anesthetic is ropivacaine at a concentration of less than 30 μmol/ml.

10. The pharmaceutical composition of claim 9, wherein said β-receptor blocker is alprenolol at a concentration of less than 15 μmol/ml.

11. The pharmaceutical composition of claim 9, wherein said β-receptor blocker is R(+) metoprolol at a concentration of less than 120 μmol/ml.

12. The pharmaceutical composition of claim 9, wherein said β-receptor blocker is S(−) metoprolol at a concentration of less than 240 μmol/ml.

13. The pharmaceutical composition of claim 11, wherein said local anesthetic is mepivacaine at a concentration of less than 120 μmol/ml.

14. The pharmaceutical composition of claim 11, wherein said β-receptor blocker is alprenolol at a concentration of less than 15 μmol/ml.

15. The pharmaceutical composition of claim 11, wherein said β-receptor blocker is R(+) metoprolol at a concentration of less than 120 μmol/ml.

16. The pharmaceutical composition of claim 11, wherein said β-receptor blocker is S(−) metoprolol at a concentration of less than 240 μmol/ml.

17. The pharmaceutical composition of claim 1, wherein said local anesthetic is bupivacaine at a concentration of less than 30 μmol/ml.

18. The pharmaceutical composition of claim 17, wherein said β-receptor blocker is alprenolol at a concentration of less than 15 μmol/ml.

19. The pharmaceutical composition of claim 17, wherein said β-receptor blocker is R(+) metoprolol at a concentration of less than 120 μmol/ml.

20. The pharmaceutical composition of claim 17, wherein said β-receptor blocker is S(+) metoprolol at a concentration of less than 240 μmol/ml.

21. The pharmaceutical composition of claim 1, wherein said local anesthetic is tocainide at a concentration of less than 120 μmol/ml.

22. The pharmaceutical composition of claim 21, wherein said β-receptor blocker is alprenolol at a concentration of less than 15 μmol/ml.

23. The composition of claim 21, wherein said β blocker is R(+) metoprolol at a concentration of less than 120 μmol/ml.

24. The composition of claim 15, wherein said β blocker is S(−) metoprolol at a concentration of less than 240 μmol/ml.

25. A method for treating a subject experiencing pain so as to produce essentially complete sensory block in the absence of substantial motor block, said method comprising administering to said patient a β-receptor blocker and a local anesthetic, wherein:
  a) said β-receptor blocker is administered in an amount sufficient to produce essentially complete sensory block in said patient when administered in combination with said local anesthetic;
  b) said local anesthetic is administered:
    i) in an amount sufficient to produce essentially complete sensory block in said patient when administered in combination with said β-receptor blocker;
    ii) in an amount lower than that needed to produce essentially complete sensory block when said local anesthetic is administered as the sole therapeutically active agent; and
    iii) with the proviso that said local anesthetic is not lidocaine.

26. The method of claim 25, wherein said β-receptor blocker is administered at a dosage lower than that needed to produce essentially complete sensory block when said β-receptor blocker is administered as the sole therapeutically active agent.

27. The method of either claim 25 or claim 26, wherein said β-receptor blocker is alprenolol.

28. The method of either claim 25 or claim 26, wherein said β-receptor blocker is R(+) metoprolol.

29. The method of either claim 25 or claim 26, wherein said β-receptor blocker is S(−) metoprolol.

30. The method of claim 25, wherein said local anesthetic is ropivacaine and is administered to said patient at a concentration of less than 30 μmol/ml.

31. The method of claim 30, wherein said β-receptor blocker is alprenolol and is administered to said patient at a concentration of less than 15 μmol/ml.

32. The method of claim 30, wherein said β-receptor blocker is the R(+) enantiomer of metoprolol administered at a concentration of less than 120 μmol/ml.

33. The method of claim 30, wherein said β-receptor blocker is the S(−) enantiomer of metoprolol administered at a concentration of less than 240 μmol/ml.

34. The method of claim 25, wherein said local anesthetic is mepivacaine and is administered to said patient at a concentration of less than 120 μmol/ml.

35. The method of claim 34, wherein said β blocker is alprenolol administered to said patient at a concentration of less than 15 μmol/ml.

36. The method of claim 34, wherein said β blocker is the R(+) enantiomer of metoprolol administered to said patient at a concentration of less than 120 μmol/ml.

37. The method of claim 34, wherein said β blocker is the S(−) enantiomer of metoprolol administered to said patient at a concentration of 240 μmol/ml.

38. The method of claim 25, wherein said local anesthetic is bupivacaine and is administered to said patient at a concentration of less than 30 μmol/ml.

39. The method of claim 38, wherein said β-receptor blocker is alprenolol administered to said patient at a concentration of less than 15 μmol/ml.

40. The method of claim 38, wherein said β-receptor blocker is the R(+) enantiomer of metoprolol administered to said patient at a concentration of less than 120 μmol/ml.

41. The method of claim 28, wherein said β-receptor blocker is the S(−) enantiomer of metoprolol administered to said patient at a concentration of less than 240 μmol/ml.

42. The method of claim 25, wherein said local anesthetic is tocainide and is administered to said patient at a concentration of less than 120 μmol/ml.

43. The method of claim 42, wherein said β-receptor blocker is alprenolol and is administered to said patient at a concentration of less than 15 μmol/ml.

44. The method of claim 42, wherein said β blocker is the R(+) enantiomer of metoprolol administered to said patient at a concentration of less than 120 μmol/ml.

45. The method of claim 42, wherein said β blocker is the S(−) enantiomer of metoprolol administered to said patient at a concentration of less than 240 μmol/ml.

* * * * *